(12) United States Patent
Dudee

(10) Patent No.: US 12,171,652 B2
(45) Date of Patent: Dec. 24, 2024

(54) CORNEAL PROSTHESIS AND METHOD OF PENETRATING KERATOPLASTY

(71) Applicant: Jitander Dudee, Lexington, KY (US)

(72) Inventor: Jitander Dudee, Lexington, KY (US)

( * ) Notice: Subject to any disclaimer, the term of this patent is extended or adjusted under 35 U.S.C. 154(b) by 416 days.

(21) Appl. No.: 17/585,933

(22) Filed: Jan. 27, 2022

(65) Prior Publication Data

US 2022/0183817 A1    Jun. 16, 2022

Related U.S. Application Data

(63) Continuation-in-part of application No. 16/572,531, filed on Sep. 16, 2019, now Pat. No. 11,324,586.

(60) Provisional application No. 62/731,260, filed on Sep. 14, 2018.

(51) Int. Cl.
*A61F 2/14*     (2006.01)
*A61F 9/008*    (2006.01)

(52) U.S. Cl.
CPC .............. *A61F 2/147* (2013.01); *A61F 2/148* (2013.01); *A61F 9/00831* (2013.01); *A61F 2220/0033* (2013.01); *A61F 2220/0075* (2013.01)

(58) Field of Classification Search
CPC ...... A61F 9/00831; A61F 2/142; A61F 2/147; A61F 2/1453
See application file for complete search history.

(56) References Cited

U.S. PATENT DOCUMENTS

| | | | | |
|---|---|---|---|---|
| 6,508,837 | B1 * | 1/2003 | Silvestrini | A61F 2/147 623/5.11 |
| 8,388,608 | B1 * | 3/2013 | Kaluzna | A61F 9/00831 606/4 |
| 2007/0244472 | A1 * | 10/2007 | Kuhn | A61F 9/008 606/4 |
| 2010/0198197 | A1 * | 8/2010 | Monteiro Carneiro | A61F 2/142 606/1 |
| 2018/0344450 | A1 * | 12/2018 | Barker | A61F 2/147 |
| 2021/0177573 | A1 * | 6/2021 | Jadidi | A61L 27/16 |

FOREIGN PATENT DOCUMENTS

WO    WO-2004041323 A2 *   5/2004  ............ A61F 2/147

\* cited by examiner

*Primary Examiner* — Javier G Blanco
(74) *Attorney, Agent, or Firm* — Black McCuskey

(57) ABSTRACT

A method of implanting the prosthesis is disclosed. The method includes forming an opening in a host tissue of an eye. The method also includes forming a perimeter of a corneal graft. The method also includes forming a first passageway through the host tissue and a second passageway through the corneal graft. The first passageway and the second passageway can have the same diameter relative to an optic axis of the eye. The method also includes aligning the first passageway and the second passageway whereby the first passageway and the second passageway are in communication with one another. The method also includes positioning a body in the first passageway and the second passageway.

2 Claims, 15 Drawing Sheets

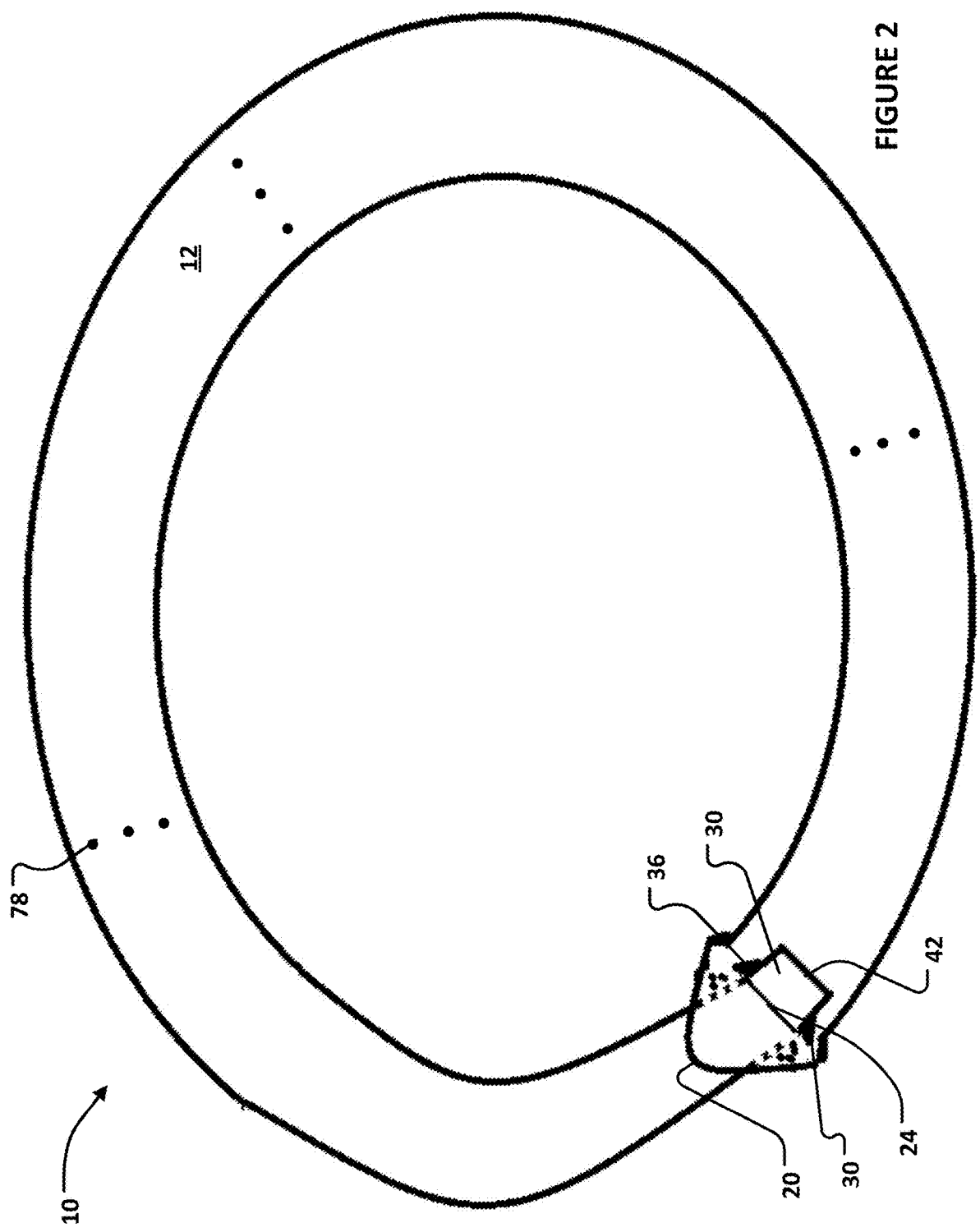

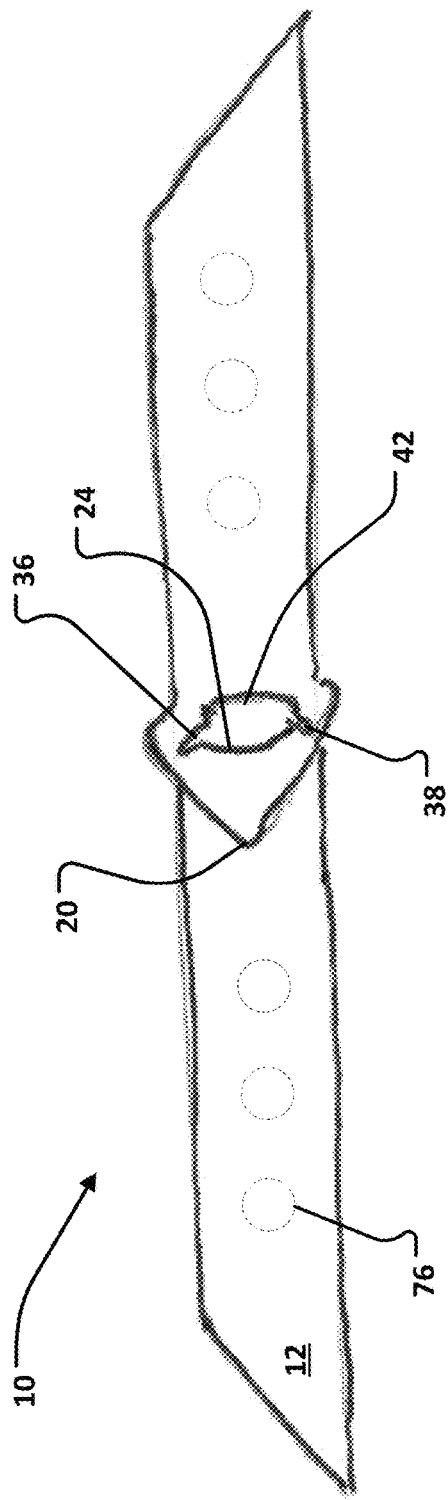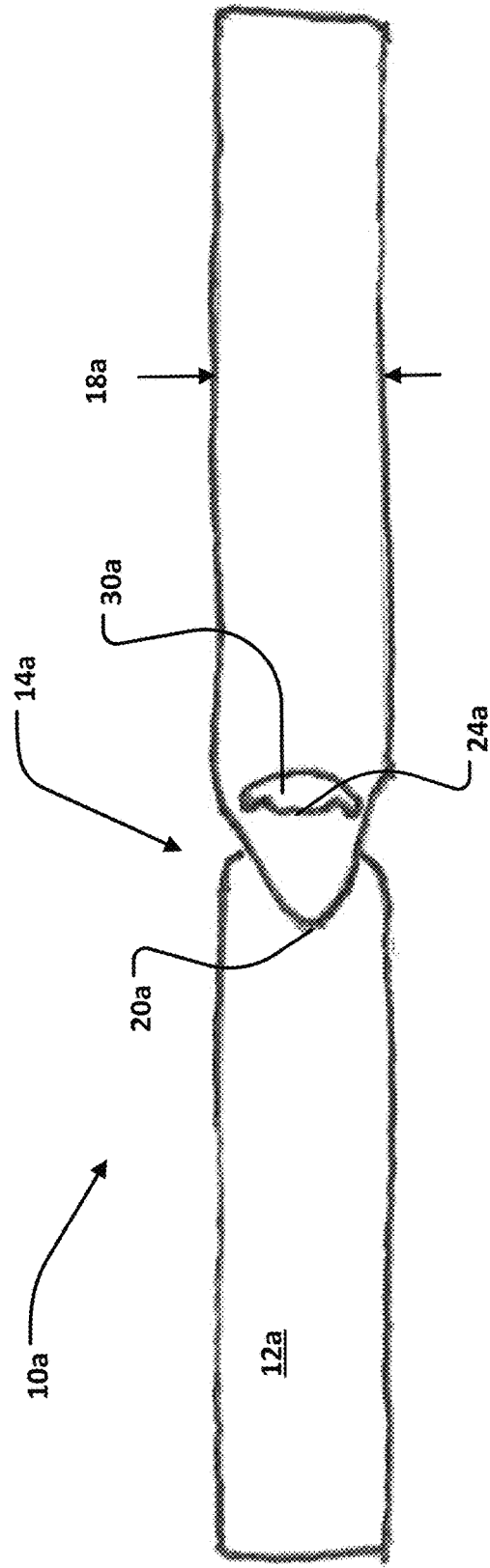

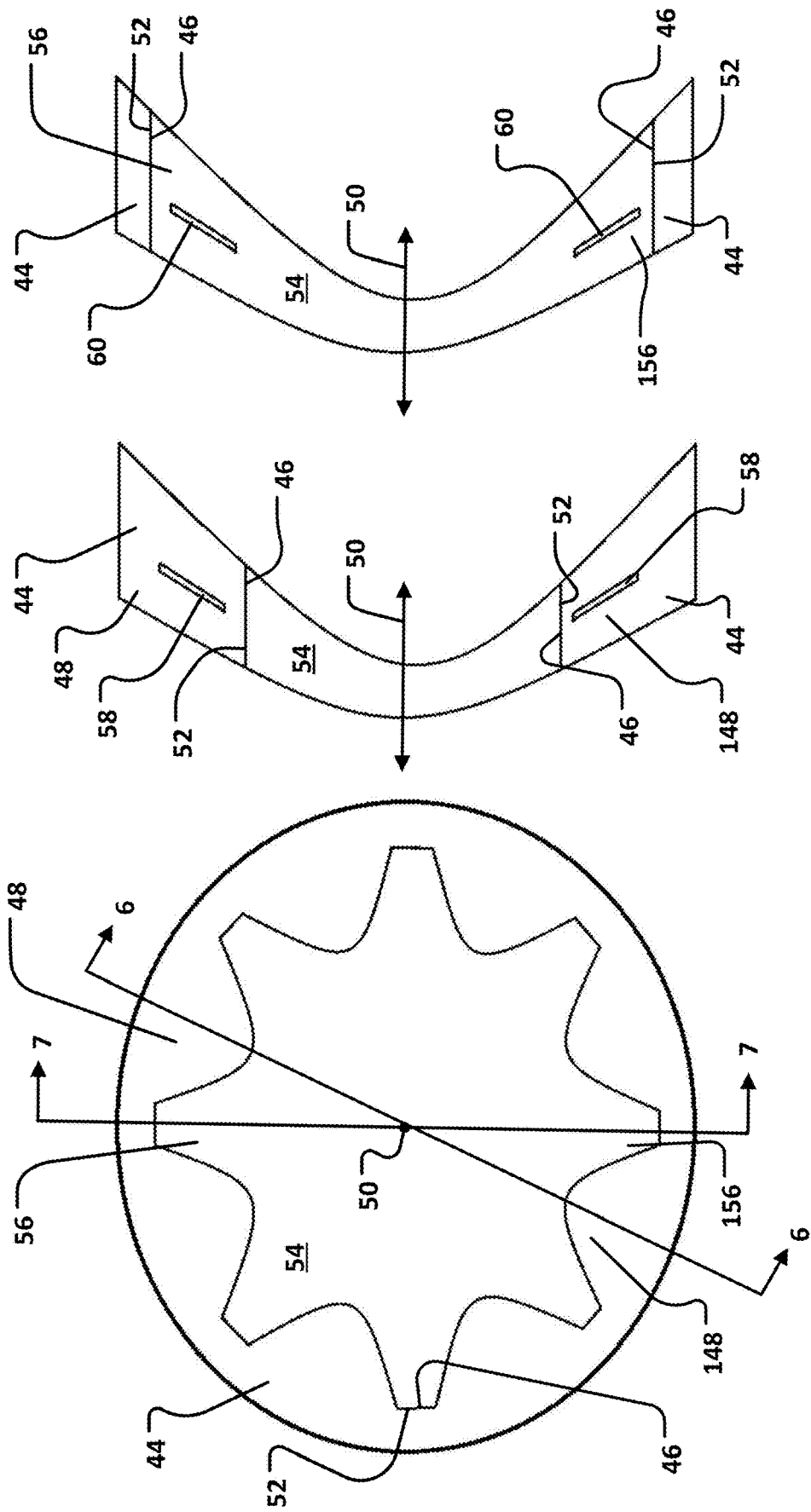

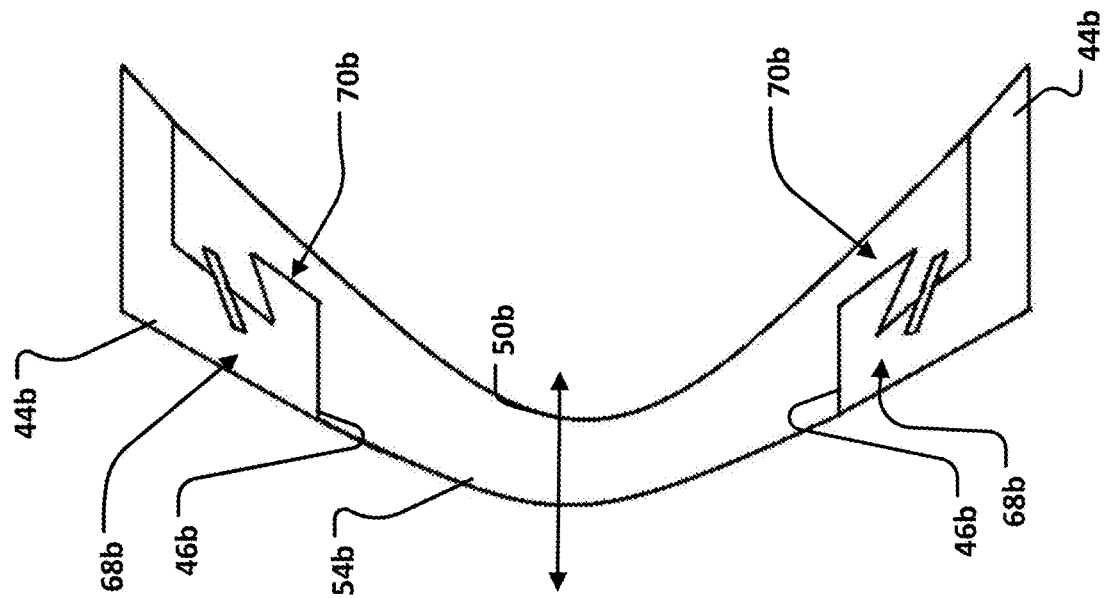
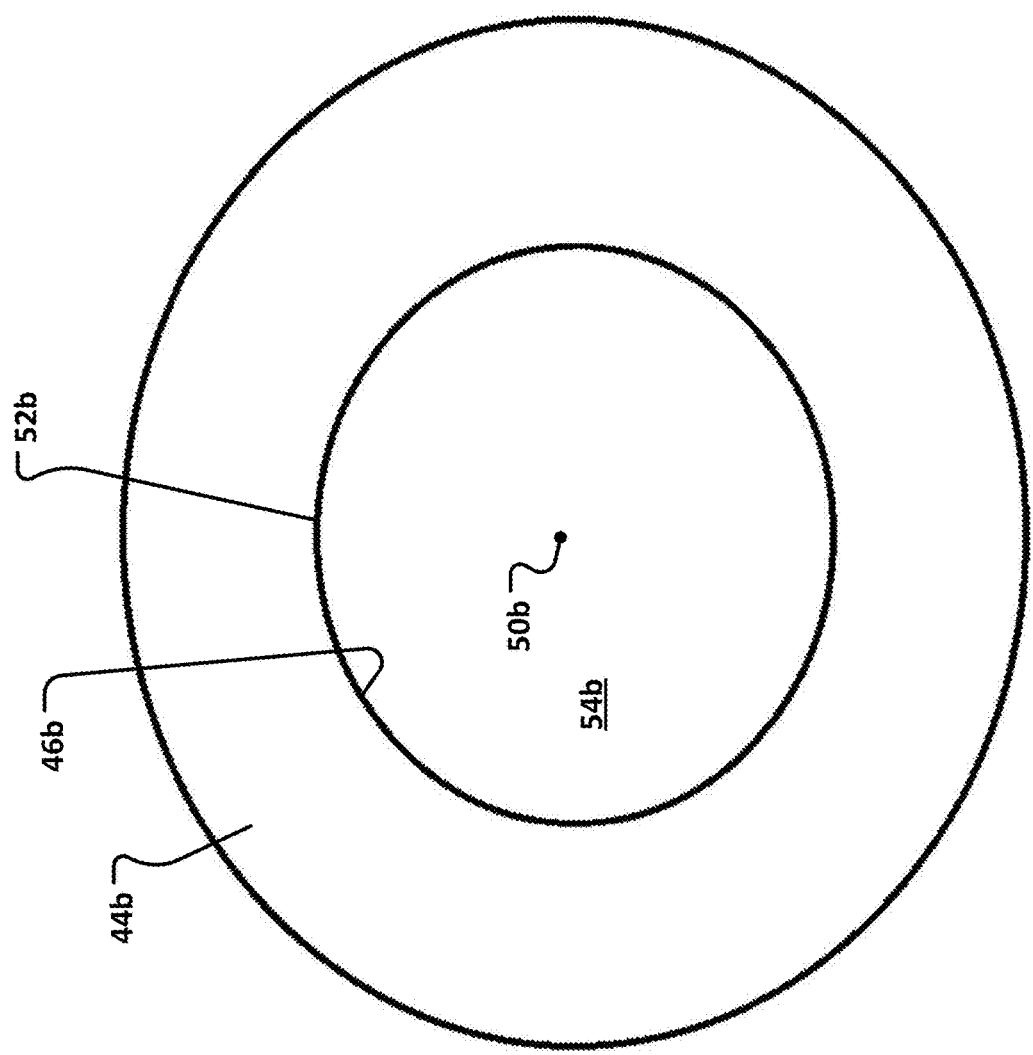

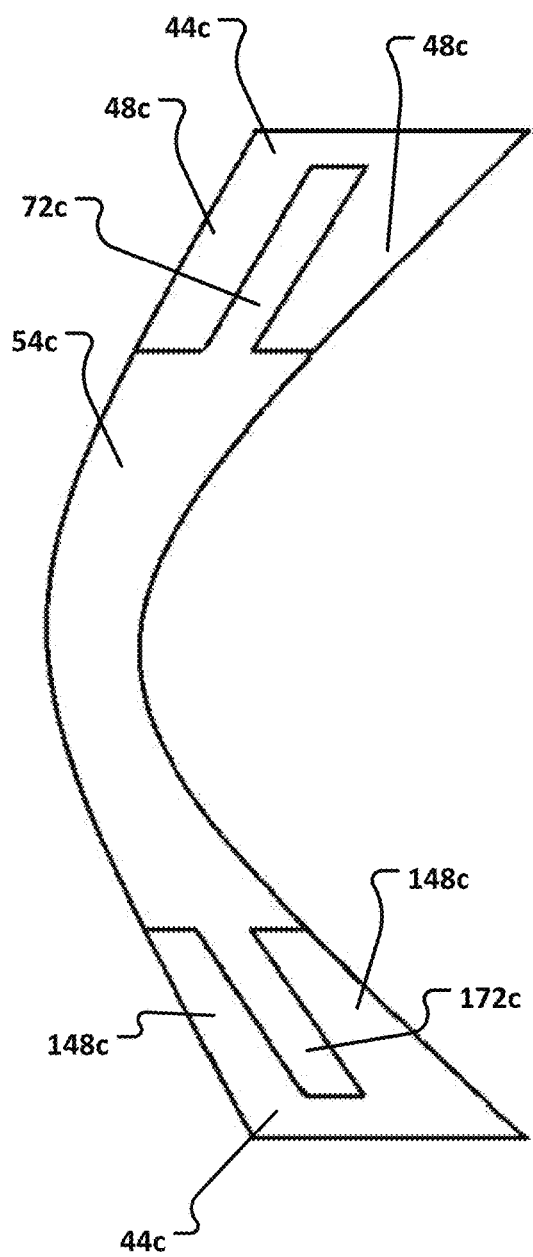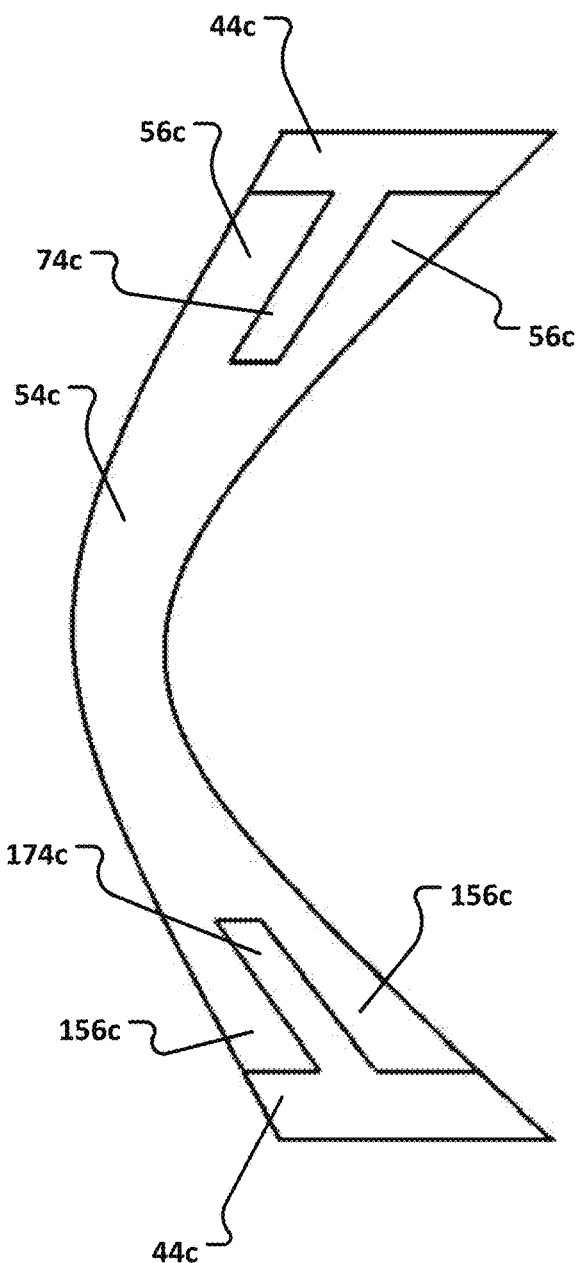
FIGURE 14
FIGURE 15

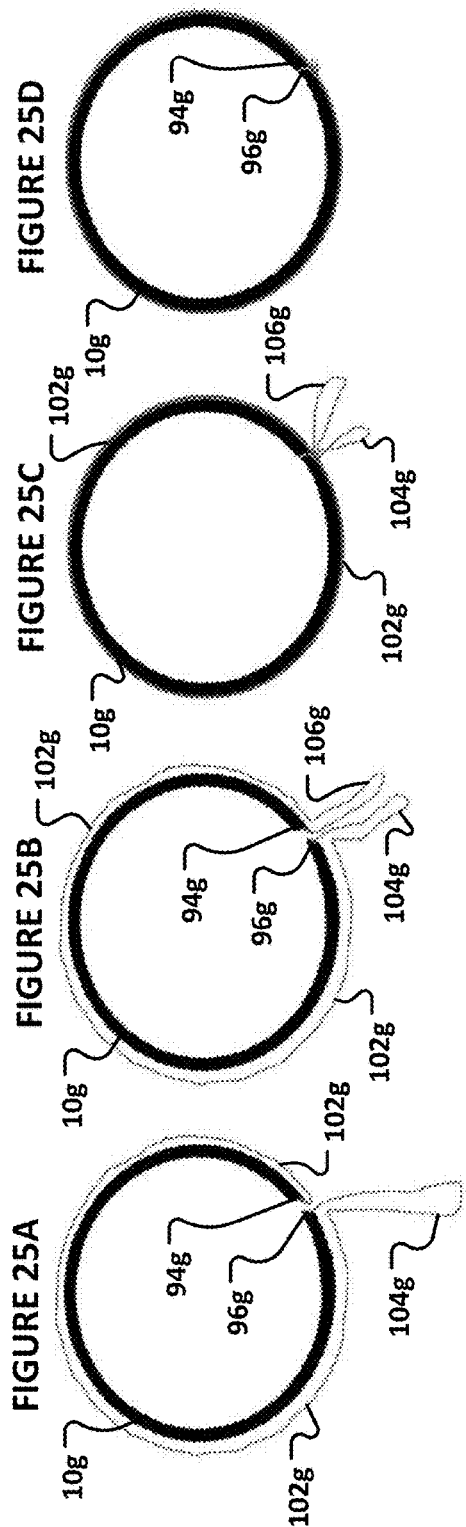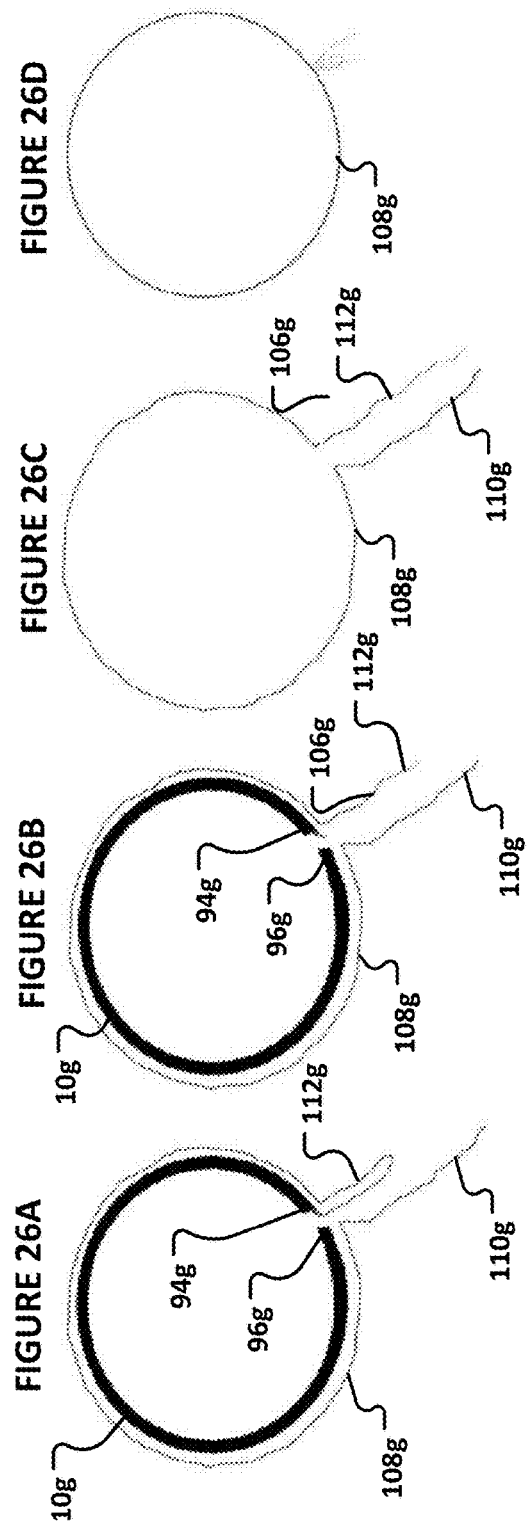

CORNEAL PROSTHESIS AND METHOD OF PENETRATING KERATOPLASTY

CROSS-REFERENCE TO RELATED APPLICATIONS

This application is a continuation-in-part of U.S. application Ser. No. 16/572,531, for a CORNEAL PROSTHESIS AND METHOD OF PENETRATING KERATOPLASTY, filed Sep. 16, 2019, which claimed the benefit of U.S. Provisional Patent Application Ser. No. 62/731,260 for a METHOD FOR CREATING DONOR AND HOST INTERFACE FOR CORNEAL TRANSPLANTATION, filed on Sep. 14, 2018, which is hereby incorporated by reference in its entirety.

BACKGROUND

1. Field

The present disclosure relates to a prosthesis for the eye and more particularly to an implant for use in penetrating keratoplasty.

2. Description of Related Prior Art

The cornea is the clear front surface of the eyeball and is responsible for the majority of the convex focusing power of the human eye. The cornea is subject to many diseases and injuries which can reduce its optical clarity and therefore replacement of the central cornea with that of a deceased donor is a common and necessary medical procedure. Such a procedure is known as corneal transplantation or penetrating keratoplasty. Some forms of corneal transplantation may only require replacement of a partial layer of the host cornea as in lamellar keratoplasty or endothelial keratoplasty. However, for many disease conditions full thickness corneal transplantation remains the only practical surgical option. Corneal transplantation is a very challenging surgery because optimal mechanical alignment of the donor tissue with the host is important to minimize inflammation that can cause a failure of the donor tissue. The interface between the host and donor tissue must have proper anatomical alignment to minimize wound disruption and induced astigmatism.

U.S. Pat. No. 8,273,121 discloses a Process of use of a device for cornea transplantation. The invention of the '121 patent is a surgical instrument (1) used in ophthalmology, which allows a penetrating or lamellar cornea transplant without the use of suture. It comprises a set of arc segments interconnected by a small diameter polypropylene wire (2), which goes through the internal body structure of each segment. The first arc segment (3), also called the segment guide, is an arc of 160-330 degrees with a circular cross-section and a rounded edge. The second arc segment (4), also called the main segment, is an arc of 270-360 degrees, and has a horizontal or oblique cross-section tangential to the surface of the cornea, or a circular cross-section. The third arc segment (5), also called the secondary segment, has a thickness or cross-section greater than that of the main segment.

U.S. Pat. No. 8,388,608 discloses a Method and implant for attachment of the transplanted cornea. The transplanted cornea attachment method of the '608 patent in eye microsurgery and the implant for attaching transplanted corneas, both donor and artificial, without the use of sutures consisting in the cutting of a fragment of the donor tissue (2) and, subsequently, the incision of the corresponding fragment (1) in the recipient tissue (3) so that the donated fragment (2) and the recipient incision (1) have teeth that interlock with each other, and the circular incision (5) in the stroma of the donor and recipient corneal stroma which is less in diameter in the donor tissue and more in diameter in the recipient tissue wherein the fastening implant (4) is subsequently inserted.

U.S. Pub. No. 2006/0100612 discloses a Laser-based device for non-mechanical, three-dimensional trepanation during cornea transplants. The laser-based device for non-mechanical, three-dimensional trepanation during cornea transplants comprises a computer-assisted control and regulation unit (4) provided with at least one control computer (5, 6, 7) and at least one display unit (8, 9), as well as a laser source (2) for generating a working laser beam (3) as well as a multi-sensor processing head (1) integrated into which are: an axial beam positioning system (11) into which the working laser beam (3) can be coupled, a focal point tracking unit (12) for the z-position displacement of the focal point (13) of the working laser beam (3) an x-y-scanner unit (14, 15) for the x and y-position displacement of the working laser beam (3), an eye position sensor unit (23, 24, 35, 36) for detection of the position of the eye, and a plasma sensor unit (16, 25) for detection of the plasma glow that occurs during the cornea trepanation.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A method of implanting the prosthesis is disclosed. The method includes forming an opening in a host tissue of an eye. The method also includes forming a perimeter of a corneal graft. The method also includes forming a first passageway through the host tissue that extends annularly about an optic axis of the eye. The method also includes forming a second passageway through the corneal graft that extends annularly about an axis of the corneal graft that is substantially collinear with the optic axis of the eye when the corneal graft is finally positioned in the eye. The first passageway and the second passageway can have the same diameter relative to the optic axis. The method also includes aligning the first passageway and the second passageway whereby the first passageway and the second passageway are in communication with one another. The method also includes positioning a body in the first passageway and the second passageway.

BRIEF DESCRIPTION OF THE DRAWINGS

The detailed description set forth below references the following drawings:

FIG. 2 is a front view of the prosthesis shown in FIG. 1 in a closed configuration;

FIG. 3 is a side view of the prosthesis shown in FIG. 1 in a closed configuration;

FIG. 4 is a side view of a prosthesis according to another exemplary embodiment of the present disclosure, wherein the prosthesis is in a closed configuration;

FIG. 5 is a front view of a portion of a host cornea and a corneal graft;

FIG. 6 is a cross-section through section lines 6-6 in FIG. 5;

FIG. 7 is a cross-section through section lines 7-7 in FIG. 5;

FIG. 12 is a front view of a portion of another host cornea and another corneal graft;

FIG. 13 is a sectional view of the host cornea and the corneal prothesis shown in FIG. 12;

FIG. 14 is a sectional view of a portion of another host cornea and another corneal prothesis;

FIG. 15 is a second sectional view of the portion of the host cornea and the corneal prothesis shown in FIG. 14;

FIG. 25A-25D illustrate a series of images associated with a second exemplary method provided by the present disclosure; and FIG. 26A-26D illustrate a series of images associated with a third exemplary method provided by the present disclosure.

DETAILED DESCRIPTION

Figure 1:
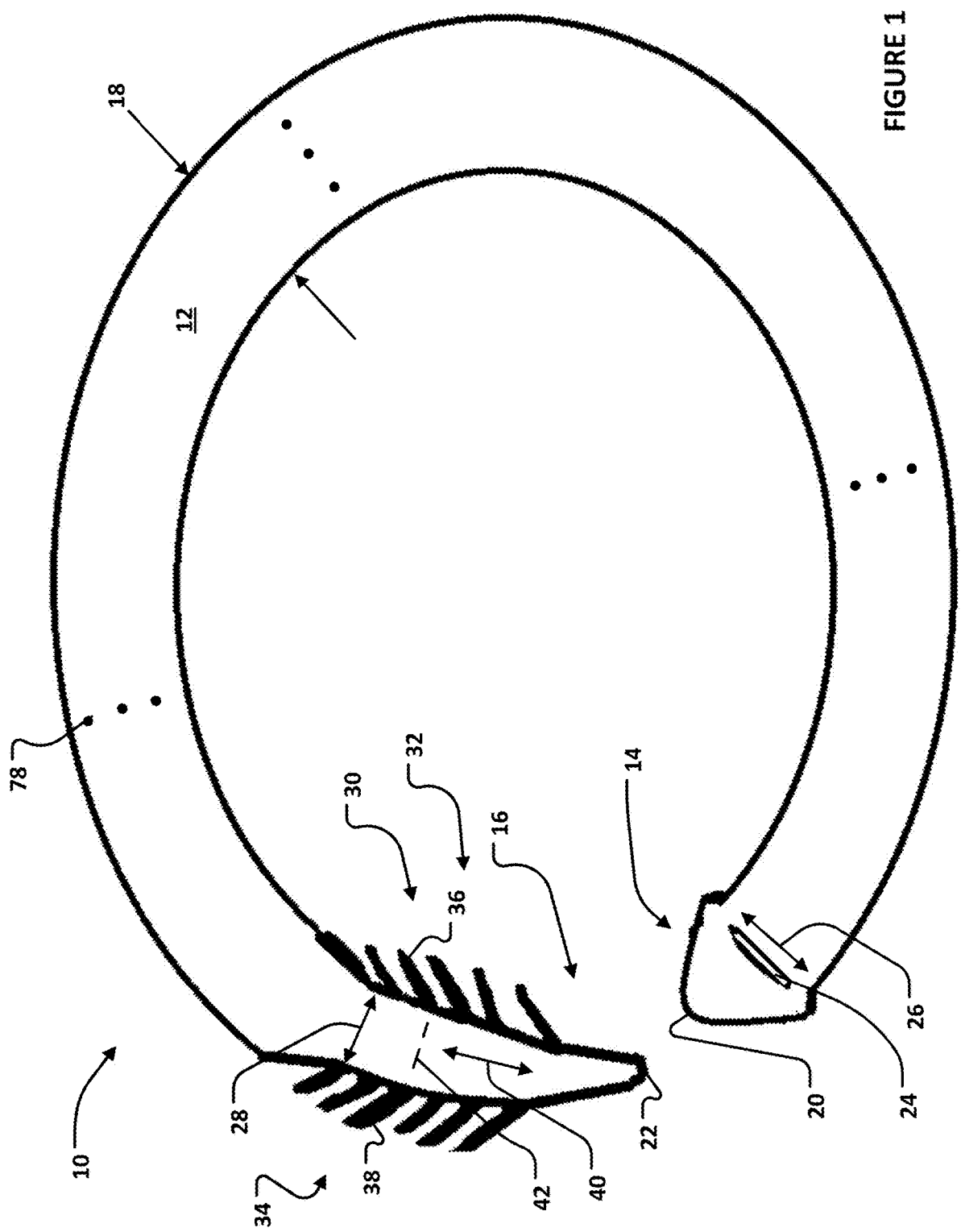
FIG. 1 is a front view of a prosthesis according to an exemplary embodiment of the present disclosure, wherein the prosthesis is in an open configuration.

A plurality of different embodiments of the present disclosure is shown in the Figures of the application. Similar features are shown in the various embodiments of the present disclosure. Similar features across different embodiments have been numbered with a common reference numeral and have been differentiated by an alphabetic suffix. Similar features in a particular embodiment have been numbered with a common two-digit, base reference numeral and have been differentiated by a different leading numeral. Also, to enhance consistency, the structures in any particular drawing share the same alphabetic suffix even if a particular feature is shown in less than all embodiments. Similar features are structured similarly, operate similarly, and/or have the same function unless otherwise indicated by the drawings or this specification. Furthermore, particular features of one embodiment can replace corresponding features in another embodiment or can supplement other embodiments unless otherwise indicated by the drawings or this specification.

The present disclosure, as demonstrated by the exemplary embodiments described below, can provide a prosthesis for use in penetrating keratoplasty that obviates the need for sutures. Referring now to FIGS. 1-3, an exemplary prosthesis 10 is configured to be implanted in a cornea of an eye to interconnect host tissue with a corneal graft. The exemplary prosthesis 10 includes a body 12 extending between a first end 14 and a second end 16. The exemplary body 12 defines a section of maximum width between the exemplary first end 14 and the exemplary second end 16. In the exemplary embodiment, the body 12 has a maximum width over most of its length and the section of maximum width is referenced at 18.

The exemplary body 12 narrows from the exemplary maximum width 18 at the exemplary first end 14 and converges to a first tip 20. The exemplary first tip 20 is hastate-shaped. The exemplary body 12 also narrows from the exemplary maximum width 18 at the exemplary second end 16 and converges to a second tip 22. The exemplary tips 20, 22 are at opposite ends of the body 12. The inner and outer edges of the body 12 can be modified from what is shown in the Figures such that one or both of the edges of the body 12 are nonplanar (not flat in a plane of cross-section) and that such edges can fit into complementary grooves in a tunnel or trench formed in host tissue 44 or the corneal graft 54. For example, the edges can include lips that protrude anteriorly and or posteriorly to allow for better fixation and easier passage through the tunnel, slit or trench. These ends can also be fashioned like bulbs in cross-section to allow for firmer fixation of the cornea.

The exemplary prosthesis 10 also includes a slit 24 defined in the exemplary body 12 at the exemplary first end 14. The exemplary slit 24 has a width, referenced at 26. A portion of the exemplary body 12, between the exemplary second tip 22 and the exemplary section 18 of maximum width, has a width, referenced at 28. The width 26 is greater than width 28. As a result, the portion of the exemplary body 12 between the exemplary second tip 22 and the exemplary section 18 of maximum width is receivable in the exemplary slit 24. In the exemplary embodiment shown in FIG. 1, this portion of the exemplary body is defined between the second tip 22 and the location that width 28 is referenced at 30. The portion 30 is the part of the exemplary body 12 that can fit in the slit 24.

The exemplary prosthesis 10 also includes a plurality of fingers including first and second sets of fingers 32, 34 projecting laterally away from the portion 30 of the exemplary body 12 between the exemplary second tip 22 and the exemplary section 18 of maximum width. The exemplary first and second sets of fingers 32, 34 project from opposite sides of the exemplary body 12. First and second individual fingers 36, 38 of the exemplary first and second sets of fingers 32, 34 respectively project laterally away from the portion 30 of the exemplary body 12 between the exemplary second tip 22 and the exemplary section 18 of maximum width. The exemplary first and second fingers 36, 38 mirroring one another across a central axis 40 of the portion 30 of the exemplary body 12 between the exemplary second tip 22 and the exemplary section 18 of maximum width. The fingers of the exemplary first and second sets of fingers 32, 34 project obliquely to the portion 30. In other embodiments, the fingers could extend perpendicular to the body 12. The fingers of the exemplary first and second sets of fingers 32, 34 are elastically deformable when the portion 30 of the exemplary body 12 between the exemplary second tip 22 and the exemplary section 18 of maximum width is passing through the exemplary slit 24. A finger can thus bend during passage of the portion 30 through the slit 24 and return to form once the finger has passed through the slit 24.

The exemplary prosthesis 10 is reconfigurable between an open or unlatched configuration and a close or latched configuration. FIG. 1 is a front view of the exemplary prosthesis 10 in the open configuration. The front view is from the same perspective as looking into the eye after the exemplary prosthesis 10 has been implanted. To reconfigure the exemplary prosthesis 10 from the open configuration to the closed configuration, the second end 22 is inserted in the slit 24 and, further, at least some part of the length of the portion 30 is drawn through the slit 24. The exemplary prosthesis 10 remains in the closed configuration through the cooperative interaction between the fingers and the slit 24. FIG. 2 is a front view of the exemplary prosthesis 10 shown in the closed configuration. FIG. 3 is a side view of the exemplary prosthesis 10 in the closed configuration. In the exemplary embodiment, the fingers 36, 38 passed through the slit 24, elastically recovered, and inhibit the portion 30 from retreating out of the slit 24. Also, in the exemplary embodiment, the portion 30 has been trimmed after passing into the slit 24. The trimmed end of the portion 30 is referenced at 42.

Referring now to FIG. 4, an exemplary prosthesis 10a is configured to be implanted in a cornea of an eye to interconnect host tissue with a corneal graft. The exemplary prosthesis 10a includes a body 12a extending between a first end 14a and a second end (similar to second end 16). An exemplary first tip 20a at the first end 14a is pointed, shaped as a "less than" mathematical symbol. The exemplary body 12a defines a section of maximum width between the exemplary first end 14a and the exemplary second end. In the exemplary embodiment, the body 12 has a maximum width over most of its length and the section of maximum width is referenced at 18a. The exemplary prosthesis 10a is configured to be cylindrical when implanted, while the exemplary prosthesis 10 is configured to be frustoconical when implanted.

The present disclosure also provides a method of implanting the exemplary prosthesis 10. The method includes forming an opening in the host tissue of the eye. Referring now to FIGS. 5-7, exemplary host tissue is referenced at 44 and an exemplary opening is referenced at 46. The exemplary opening 46 in the exemplary host tissue 44 has been formed to include a first plurality of flaps in the exemplary host tissue 44. Two of the flaps are referenced at 48, 148 and the flaps are positioned about an optic axis 50 of the eye. The flaps extend toward the optic axis 50.

The method also includes forming a perimeter of the corneal graft to correspond to the exemplary opening 46 in the exemplary host tissue 44 such that the exemplary corneal graft 54 is receivable in the exemplary opening 46. Referring still to FIGS. 5-7, an exemplary perimeter is referenced at 52 and an exemplary corneal graft is referenced at 54. The exemplary perimeter 52 has been formed to include a second plurality of flaps in the exemplary corneal graft 54 positioned about the optic axis. Two of the flaps are referenced at 56, 156 and the flaps are positioned about the optic axis 50 of the eye. The flaps extend away from the optic axis 50 when the exemplary corneal graft 54 is finally positioned in the eye. In the embodiment reflected in FIGS. 5-7, the exemplary corneal graft 54 is fully received in the exemplary opening 46. As shown in FIGS. 6 and 7, the edges of the exemplary corneal graft 54 are flush with the edges of the exemplary opening 46 and the edges of the host tissue 44.

The method also includes forming a first passageway through the exemplary host tissue 44 that extends annularly about the optic axis 50 of the eye. An exemplary first passageway is referenced at 58 in FIG. 6. The exemplary first passageway 58 comprises discontinuous tunnel portions, each extending through one of the first plurality of flaps of the host tissue 44. The method also includes forming a second passageway through the exemplary corneal graft 54 that extends annularly about an axis of the exemplary corneal graft 54 that is substantially collinear with the optic axis 50 of the eye when the exemplary corneal graft 54 is finally positioned in the eye. An exemplary second passageway is referenced at 60 in FIG. 7. The exemplary second passageway 60 includes discontinuous tunnel portions, each extending through one of the second plurality of flaps. The passageways 58, 60 can be formed with a femtosecond laser.

The method also includes aligning the first passageway and the second passageway whereby the first passageway and the second passageway are in communication with one another. In the exemplary embodiment, this can be accomplished by inserting the exemplary corneal graft 54 into exemplary opening 46 of the exemplary host tissue 44 such that the first plurality of flaps and the second plurality of flaps circumferentially and alternatingly overlap about the optic axis when the exemplary corneal graft 54 is finally positioned in the eye. The portions of the second passageway 60 in the second plurality of flaps line up with the portions of the first passageway 58 in the first plurality of flaps.

The method also includes positioning the exemplary body 12 concurrently in the first passageway 58 and the second passageway 60. In the exemplary embodiment, the body 12 can be woven into the first and second plurality of flaps. The first tip 20 be successively directed through each tunnel portion in each flap until the body 12 extends through every tunnel portion.

The method also includes directing the exemplary second tip 22 through the exemplary slit 24. The exemplary second tip 22 can be directed through the exemplary slit 24 until at least one of the first set of fingers and at least one of the second set of fingers pass through the exemplary slit 24. The length of the portion 30 that is drawn through the slit 24 is chosen as desired, such as to optimize the tightness or tautness of the interconnection between the host tissue 44 and the corneal graft 54. Thus, in some operating environments, it may be desirable that a plurality of the first set of fingers and a plurality of the second set of fingers pass through the exemplary slit 24. In the exemplary embodiment, the portion 30 is directed through the slit 24 after the body 12 is positioned in the first and second passageways 58, 60 and after the first and second passageways 58, 60 are aligned.

FIGS. 8-11 correspond to exemplary method of implanting the exemplary prosthesis 10a. The method includes forming an opening in the host tissue of the eye. As referenced in FIGS. 8 and 9, an exemplary opening 46a has been formed in the exemplary host tissue 44a. Dashed lines 62a and 64a reference the outer and inner profiles of the portion of the host tissue 44a that has been removed.

Figure 8:
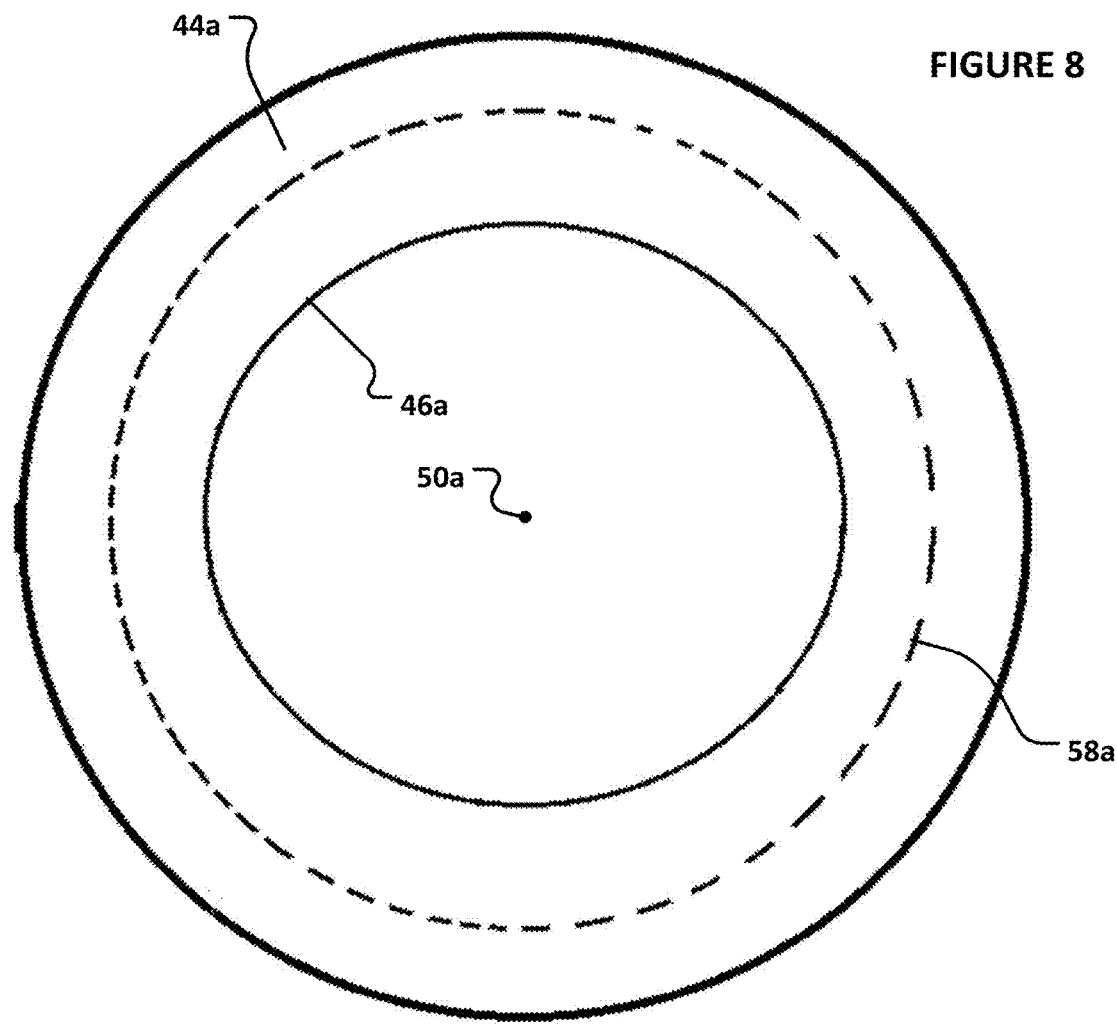
FIG. 8 is a front view of a portion of another host cornea.
Figure 9:
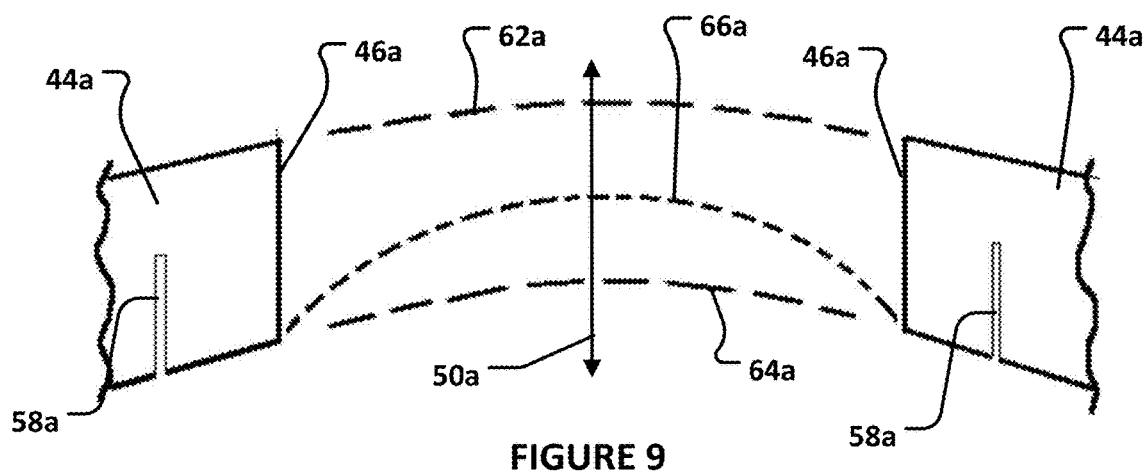
FIG. 9 is a sectional view of the portion shown in FIG. 8.
Figure 10:
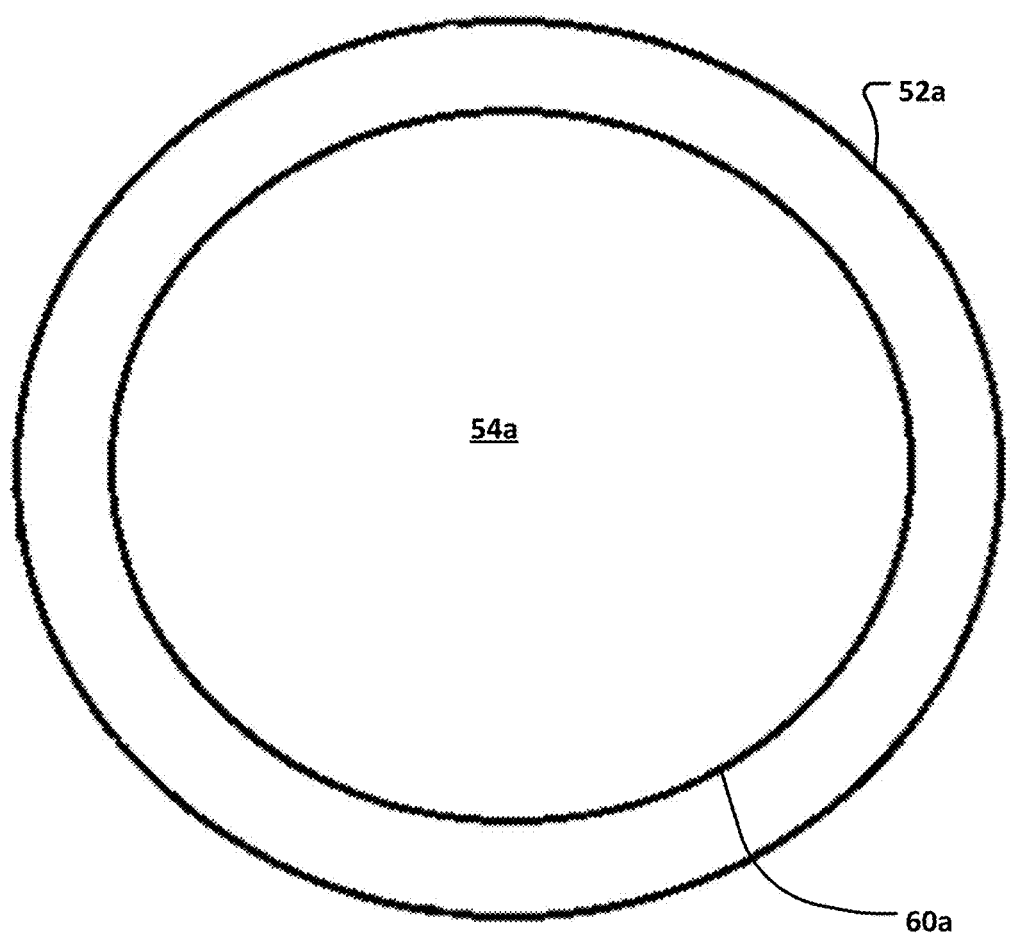
FIG. 10 is a front view of another corneal graft.
Figure 11:
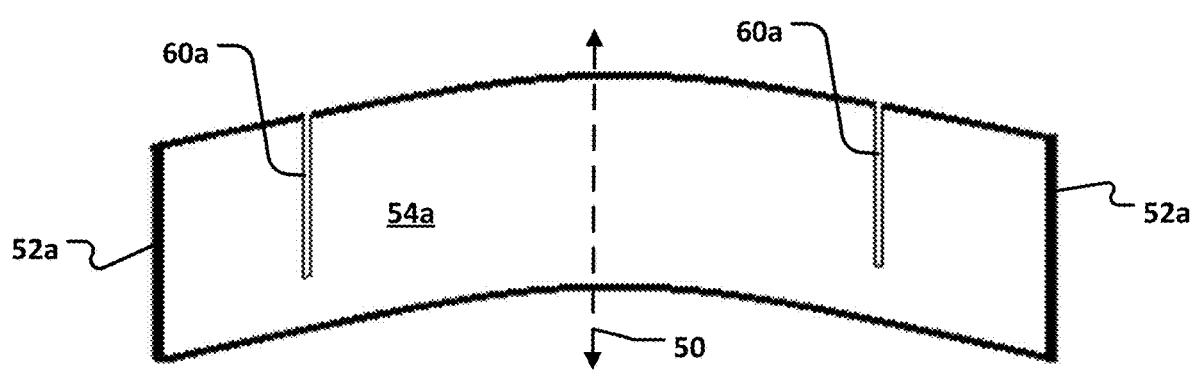
FIG. 11 is a sectional view of the corneal graft shown in FIG. 10.

The method also includes forming a perimeter of the corneal graft. As shown in FIGS. 8 and 9, an exemplary perimeter is referenced at 52a and an exemplary corneal graft is referenced at 54a. In the embodiment reflected in FIGS. 5-7, the exemplary corneal graft 54 is fully received in the exemplary opening 46. As will be described, in the embodiment reflected in FIGS. 8-11, the exemplary corneal graft 54a is partially received in the exemplary opening 46a.

The method also includes forming a first passageway through the exemplary host tissue 44a that extends annularly about the optic axis 50a of the eye. An exemplary first passageway is referenced at 58a in FIGS. 8 and 9. The exemplary first passageway 58a comprises continuous trench formed into an external surface of the exemplary host tissue 44a.

The method also includes forming a second passageway through the exemplary corneal graft 54a that extends annularly about an axis of the exemplary corneal graft 54a that is substantially collinear with the optic axis 50a of the eye when the exemplary corneal graft 54a is finally positioned in the eye. The position of the optic axis 50a relative to the corneal graft 54a when the exemplary corneal graft 54a is finally positioned in the eye is shown in dashed line in FIG. 11. An exemplary second passageway is referenced at 60a in FIGS. 10 and 11. The exemplary second passageway 60a includes a continuous trench formed into an external surface of the exemplary corneal graft 54a. The passageways 58a, 60a can be formed with a femtosecond laser.

The method also includes aligning the first passageway and the second passageway whereby the first passageway and the second passageway are in communication with one another. In the exemplary embodiment, this can be accomplished by first locating the exemplary body 12a fully in the first passageway 58a. The exemplary corneal graft 54 can then be moved through the opening 46a and progressively adjusted to slip the second passageway 60a over the exemplary body 12a, which projects out of the first passageway 58a along the axis 50a.

The method also includes directing the exemplary second tip of the body 12a through the exemplary slit 24a. The exemplary second tip can be directed through the exemplary slit 24a until at least one of the first set of fingers and at least one of the second set of fingers pass through the exemplary slit 24a. The length of the portion 30a that is drawn through the slit 24a is chosen as desired, such as to optimize the tightness or tautness of the interconnection between the host tissue 44a and the corneal graft 54a. Thus, in some operating environments, it may be desirable that a plurality of the first set of fingers and a plurality of the second set of fingers pass through the exemplary slit 24a. It is noted that the line 66a in FIG. 9 represents, in exaggerated form, the outer surface of the corneal graft 54a after completion of the method. It is noted that swollen tissue in the eye can enhance the interconnection between the host tissue 44a and the graft 54a.

FIGS. 12 and 13 correspond to exemplary method of implanting the exemplary prosthesis 10. An exemplary opening 46b has been formed in exemplary host tissue 44b to include a first undercut 68b extending circumferentially about an optic axis 50b. An undercut is a structural feature in which material has been cut away from the underside of a structure so as to leave an overhanging portion in relief. An exemplary perimeter 52b has been formed in a corneal graft 54b to include a second undercut 70b extending circumferentially about the optic axis 50b. First and second passageways have also been formed, similar to the passageways 58, 60, but cylindrically-shaped rather than frustoconical. The undercuts 68b, 70b are received in one another when the exemplary corneal graft 54a is finally positioned in the eye. The undercuts 68b, 70b can be formed with a femtosecond laser.

FIGS. 14 and 15 correspond to exemplary method of implanting the exemplary prosthesis 10 or the exemplary prosthesis 10a. FIG. 14 is a cross-section taken in a similar plane to the plane shown in FIG. 6 and FIG. 15 is a cross-section taken in a similar plane to the plane shown in FIG. 7. The flaps shown in the embodiment of FIGS. 5-7 have been further modified such the flaps circumferentially and alternatingly overlap about the optic axis and also overlap along the optic axis when the exemplary corneal graft 54c is finally positioned in the eye. Host tissue 44c includes flaps 48c and 148c. Each of the flaps 48c, 148c has been further shaped to include outer and inner portions by removing a middle portion. The empty middle portions have been filled by portions 72c, 172c of a corneal graft 54c. Similarly, flaps 56c, 156c of the corneal graft 54c has been further shaped to include outer and inner portions by removing a middle portion. The empty middle portions of the corneal graft 54c have been filled by portions 74c, 174c of the host tissue 44c.

Figure 16:
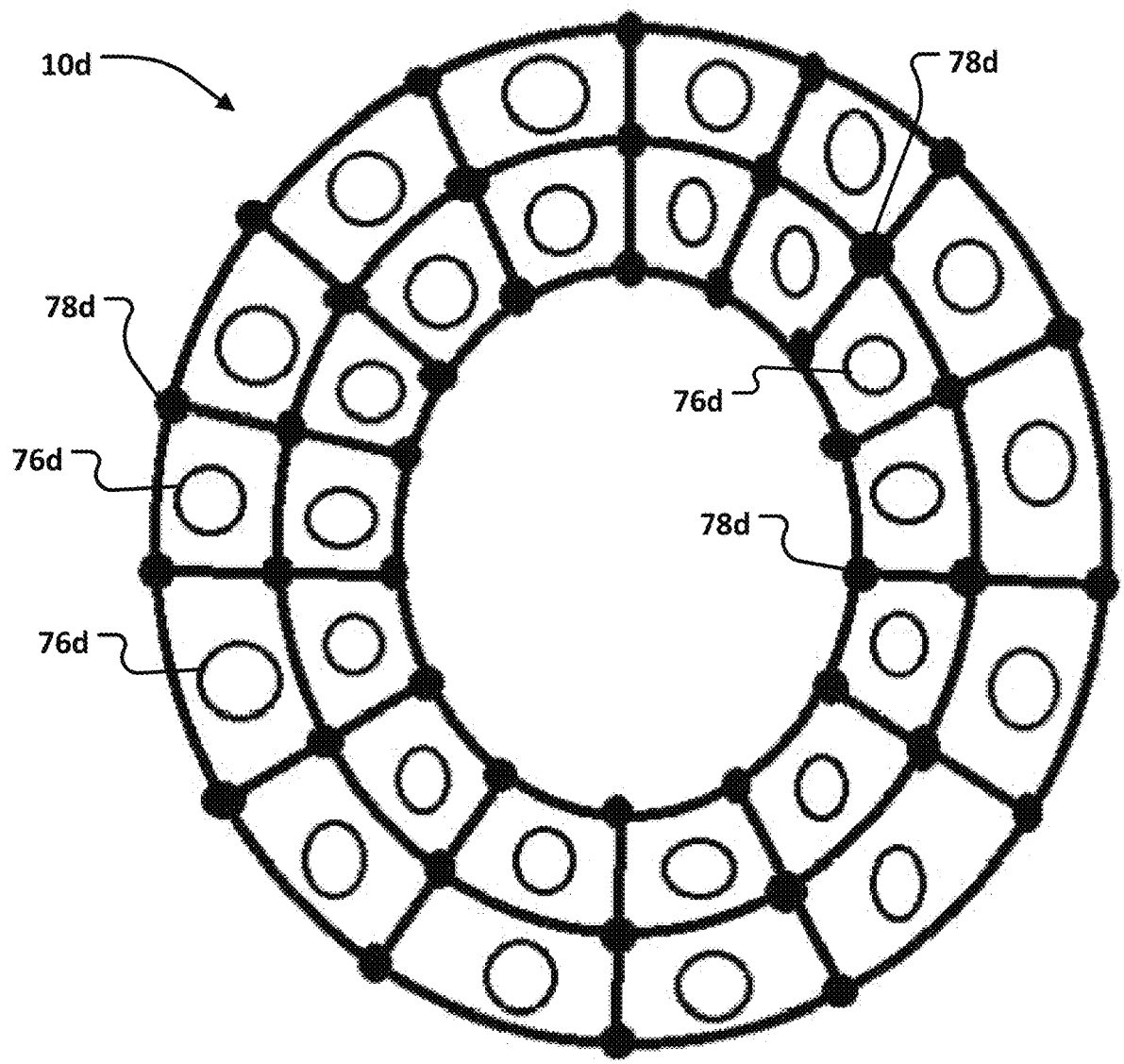
FIG. 16 is a front view of a prosthesis according to another embodiment of the present disclosure.
Figure 17:
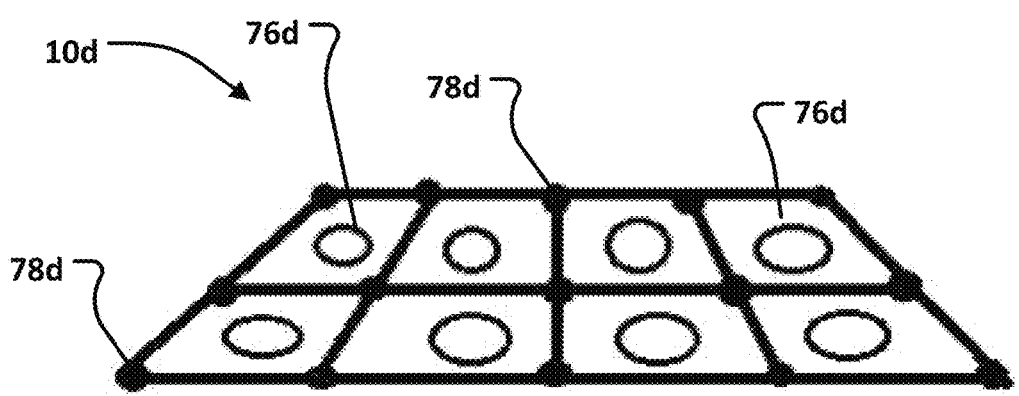
FIG. 17 is a side view of the prosthesis shown in FIG. 16.

In one or more embodiments of the present disclosure, the prosthesis may include fenestration (one or more perforations in the structure), as shown in FIG. 3 in phantom and referenced at 76. Fenestration would be beneficial both to permit corneal healing at the interface and allow diffusion of oxygen to the central cornea. Fenestration in the prosthesis can be subject to postoperative modulation by applied electromagnetic energy (such as a laser) to change tension in shape within the band and adjust for refractive properties of the cornea once the stable refractive outcome can be assessed postoperatively. In one or more embodiments of the present disclosure, the prosthesis can include elements visible on the outer surface that can be subject to postoperative modulation by applied electromagnetic energy to alter the shape of the prosthesis and thus change tension within the band. Examples are referenced in FIGS. 1 and 2 at 78. This can be done to adjust for refractive properties of the cornea once the stable refractive outcome can be assessed postoperatively. FIGS. 16 and 17 disclose an embodiment of the present disclosure in which a continuous prosthesis 10d is frustoconical and includes fenestrations 76d and elements 78d to be subjected to laser energy.

In embodiments of the present disclosure in which the prosthesis is circular, it may be desirable that the shape of the graft (also known as the "donor button") can be undulating or petaloid, as shown in FIG. 5. If the shape of the donor button is circular, as might be necessitated if replacing a failed circular graft, or if inserting a keratoprosthesis, then the prosthesis itself can be continuous and/or noncircular in order to pass through both recipient tissue and foreign implant/transplant. Such a shape may be a circular zigzag (such as a Star of David) or a circle with an undulating circumference (a wavy, circular perimeter). If the prosthesis is to be threaded through a tunnel, a rigid, discontinuous circle can be desirable. If it is to be inserted into a trench incision (as shown in FIGS. 8-11) then either a circular zigzag or a circle with an undulating circumference can be a desirable shape.

In various embodiments of the present disclosure, the prosthesis can slip into the trench in the donor tissue so that the corneal epithelium will go back over it and that the prosthesis in the recipient tissue would not protrude beyond the inner endothelial cell layer and thus not disrupt the normal physiology of the cornea and anterior chamber. Since the thickness of the cornea at this junction would be approximately five hundred μm, a trench depth of about two hundred and fifty μm in both the underside of the recipient and top surface of the donor tissue would seem desirable and thus limit the vertical height of the prosthesis to about two hundred μm or less. A prosthesis of one hundred μm thickness should have ample strength. However, materials such as titanium or other biocompatible could provide both the rigidity and strength to a smaller prosthesis in order to be handled and placed without damage. There are also biocompatible aerogels which have enormous strength with limited brittleness.

In one or more embodiments of the present disclosure, the method of forming circumferential suture tracks through the host and/or donor tissue can include using a femtosecond laser. The tracks may be of multiple sets of varying diameter. Although the present disclosure provides methods and structures tending to minimize the need for sutures, pre-placement of suture tracks in such a manner that makes suture placement faster and more accurate and use less suture material and the less traumatic needle can be included with various embodiments of the present disclosure. It is noted that only one knot may be needed to be tied each set of sutures at a particular diameter.

In one or more embodiments of the present disclosure, a prosthesis can contain a depot of slow-release medication such as steroids and antibiotic to facilitate healing, especially in the fenestrations described above. Another medication that would be useful would be preparations such as vitamin A which are activated by ultraviolet light to promote a process known as collagen cross-linking which has beneficial effects in many corneal diseases and strengthens the cornea. The drug depot reservoir function can be desirable for a) collagen cross-linking, b) immunosuppressants to prevent rejection, and c) antibiotics to prevent infection.

Figure 18:
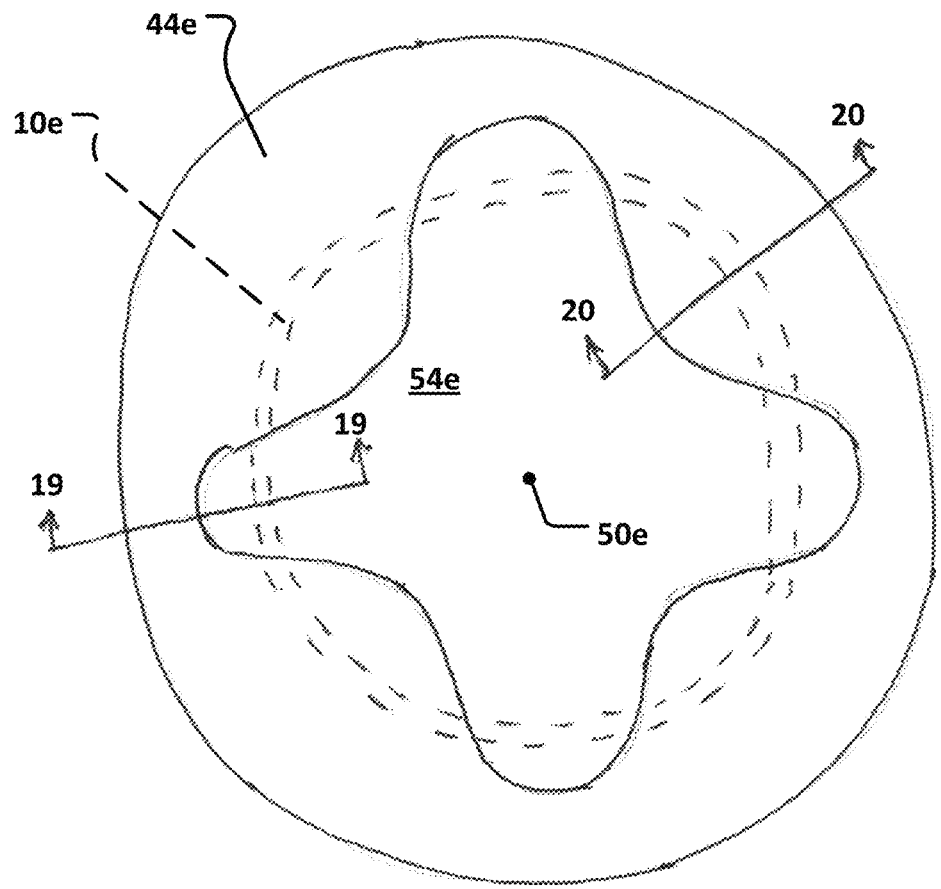
FIG. 18 is a front view of a portion of a host cornea and a corneal graft according to another embodiment of the present disclosure.
Figure 19:
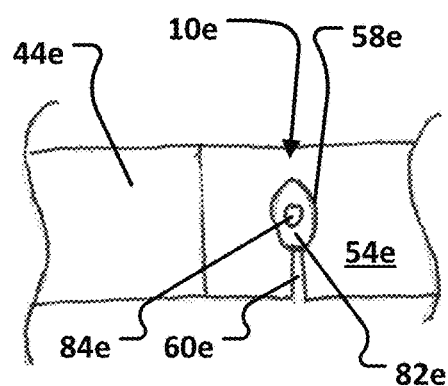
FIG. 19 is a cross-section through section lines 19-19 in FIG. 18.
Figure 20:
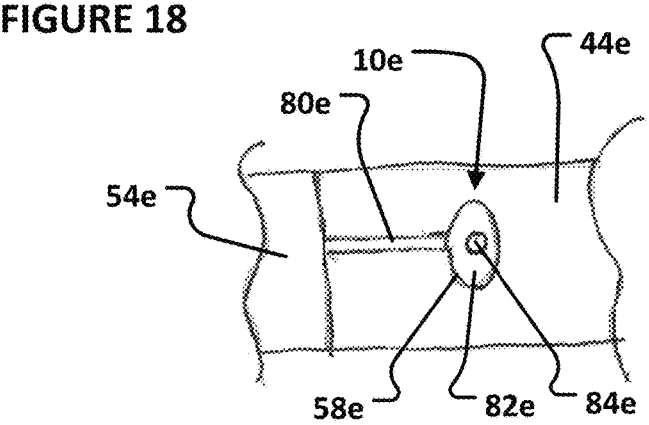
FIG. 20 is a cross-section through section lines 20-20 in FIG. 18.

FIGS. 18-20 illustrate another embodiment of the present disclosure. Host tissue 44e has received a corneal graft 54e and the interface has been shaped with interlocking flaps or petals. A prosthesis 10e is passing through a discontinuous tunnel 58e in the host tissue 44e and is received in a discontinuous trench 60e formed in the corneal graft 54e. The appearance of the prosthesis 10e in FIG. 18 shows the discontinuous tunnel 58e (a first passageway) and the discontinuous trench 60e (a second passageway) have the same diameter relative to an optic axis 50e. Thus, the flaps of the corneal graft 54e are draped over the portions of the prosthesis 10e that are exposed between adjacent flaps of the host tissue 44e. As shown by FIG. 20, the discontinuous tunnel 58e in the host tissue 44e has been formed to include a laterally extending gap (referenced at 80e) to the tunnel 58e in order to allow the prosthesis 10e to be continuous and inserted in the host tissue 44e more easily. Thus, a prosthesis according to the present disclosure can either be fully closed prior to implantation (i.e. constructed as a continuous loop) as shown in FIGS. 18-20 or can be closed after positioning as exemplified by the embodiment shown in FIG. 1.

FIGS. 19 and 20 also illustrate another embodiment of a prosthesis of the present disclosure. The prosthesis 10e is generally circular or ellipsoid in cross-section and includes an outer layer 82e and an inner layer 84e. The layers 82e, 84e are formed from different materials. The material used for layer 82e can be responsive to laser energy of a first wavelength, to expand or contract. The material used for layer 84e can be responsive to laser energy of a second wavelength different from the first wavelength, to expand or contract. The material used for layer 82e can be unresponsive to laser energy of the second wavelength and the material used for layer 84e can be unresponsive to laser energy of a first wavelength. Thus, one of the layers 82e, 84e could be modified with laser energy to shrink and thereby tighten the interconnection between the host tissue 44e and the corneal graft 54e while the other could be modified with laser energy to expand and thereby loosen the interconnection between the host tissue 44e and the corneal graft 54e.

Figure 21:
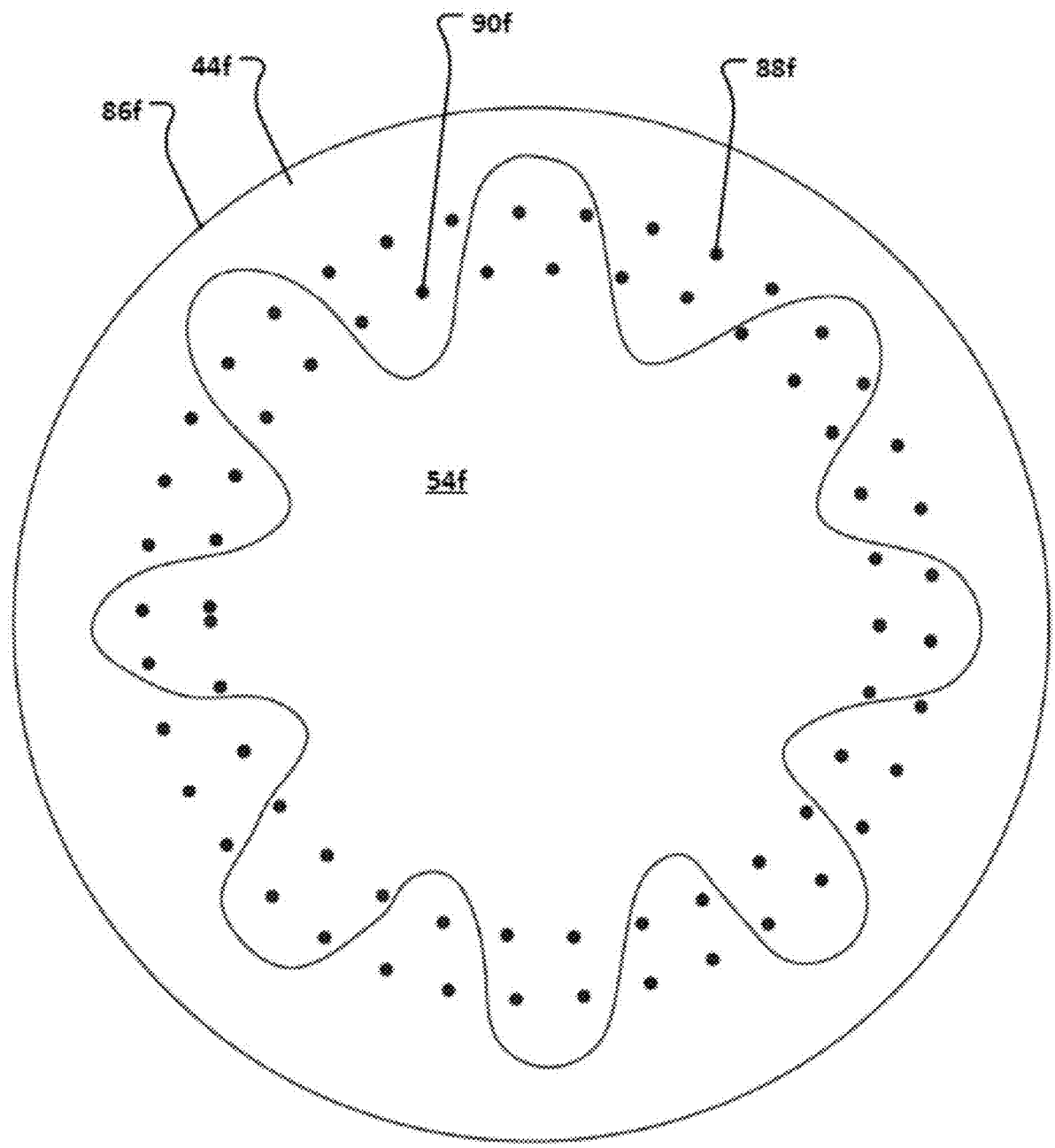
FIG. 21 is a front view of a portion of a host cornea and a corneal graft according to another embodiment of the present disclosure.
Figure 22:
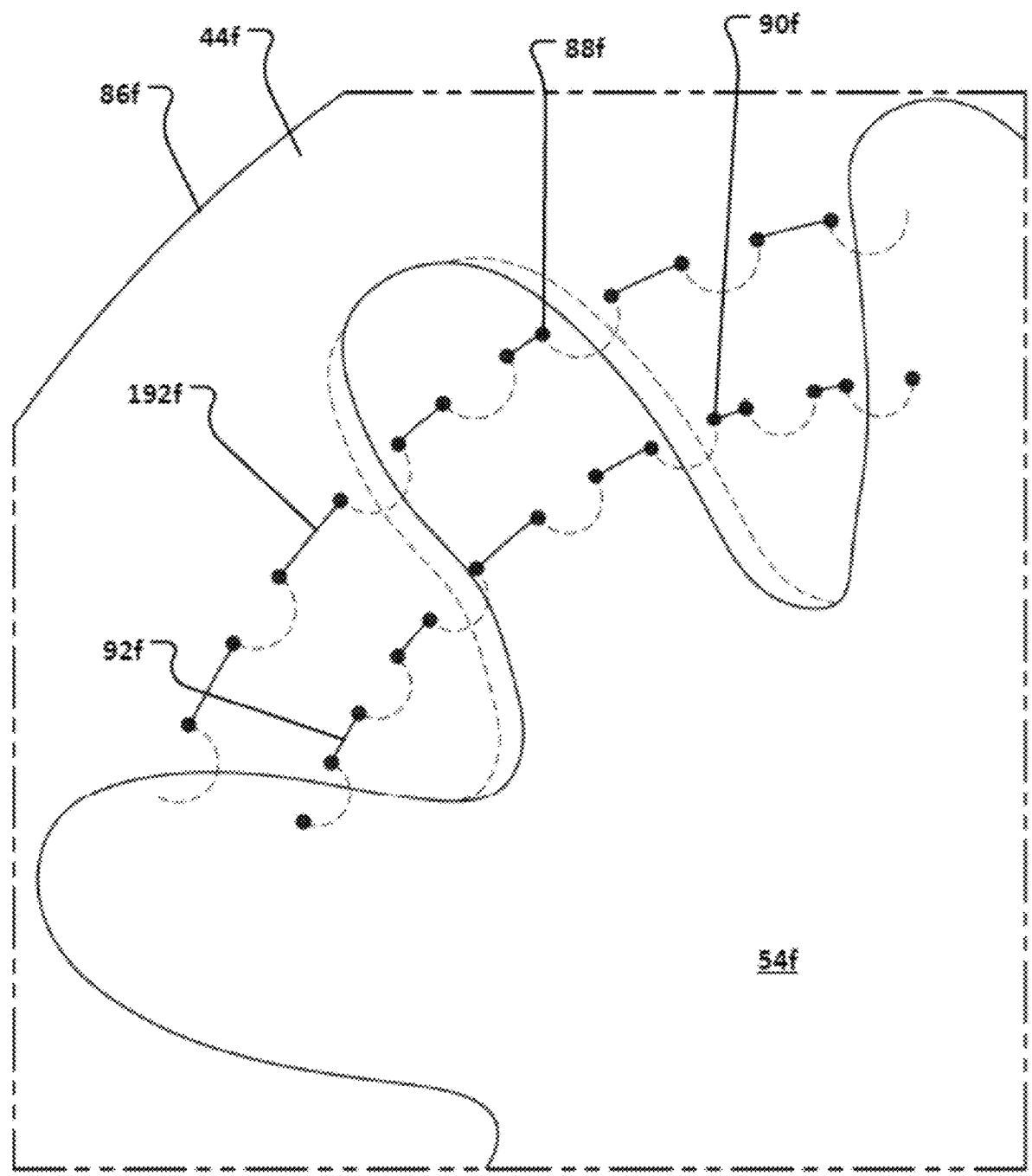
FIG. 22 is a magnified and perspective view of a portion of the structures shown in FIG. 21.

FIGS. 21 and 22 illustrate another embodiment of the present disclosure. Host tissue 44f has received a corneal graft 54f and the interface has been shaped with interlocking flaps or petals. It is noted that an arbitrary outer boundary of the host tissue 44f is referenced at 86f In FIG. 21, patterns of suture tracks have been formed by a femtosecond laser in the host tissue 44f and the corneal graft 54f. These suture tracks are illustrated as dots and an outer pattern includes suture tracks such as referenced at 88f and an inner pattern includes suture tracks such as referenced at 90f Sutures can be used in conjunction with a prosthesis. FIG. 22 shows sutures 92f, 192f extending through and between suture tracks. FIG. 22 also shows a portion of the path taken by each suture 92f, 192f, with the sutures 92f, 192f represented in phantom when passing below the surface. It can be desirable to complete and tie the outer suture 192f first for stability and then adjust the tightness of the inner suture 92f as desired. Including the sutures 92f, 192f can be desirable to inhibit astigmatism. It can be desirable to reduce the distance between the suture and the corneal periphery in order to reduce corneal inflammation and neovascularization.

Figure 23:
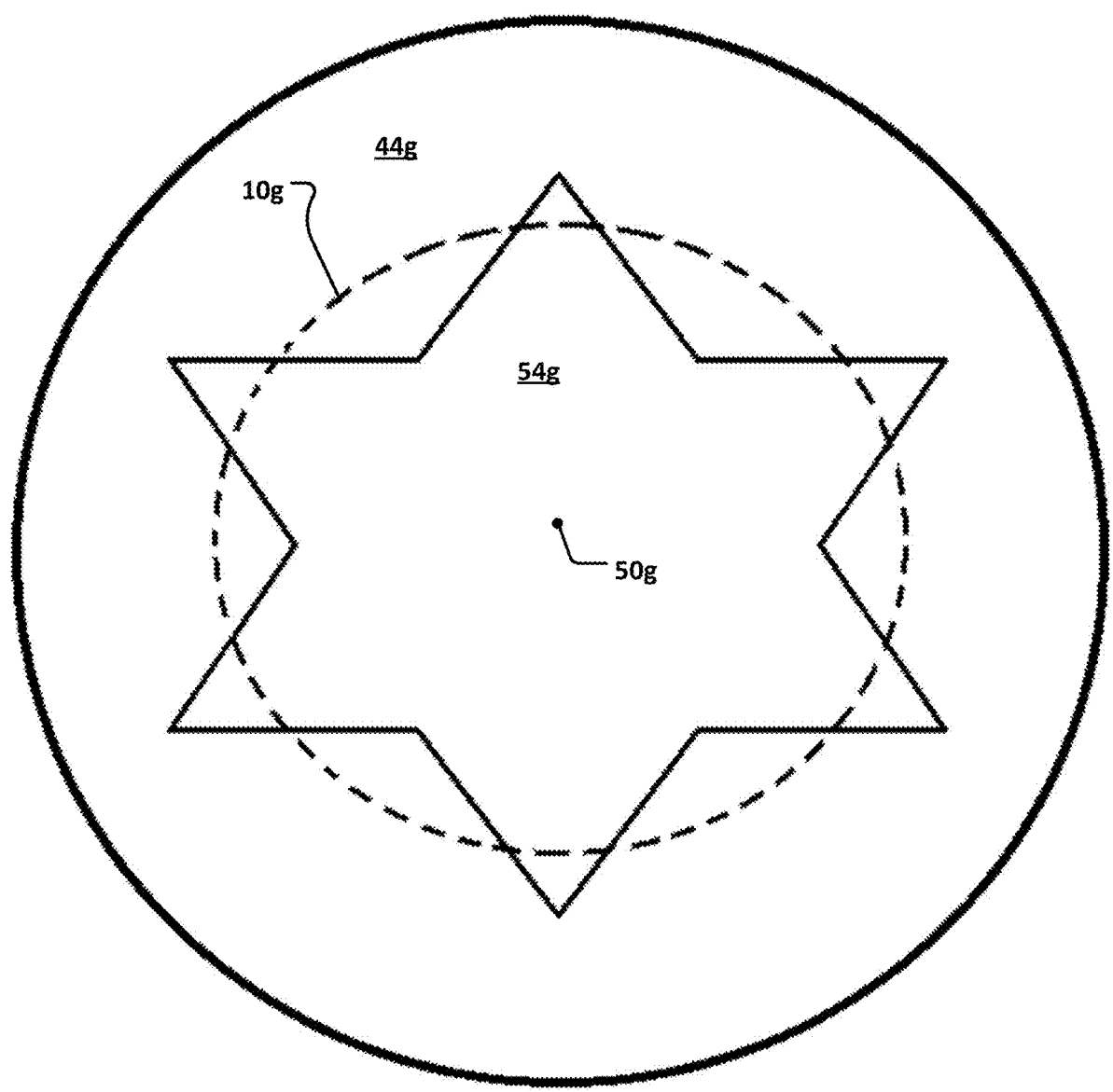
FIG. 23 is a front view of a portion of a host cornea and a corneal graft.
Figure 24:
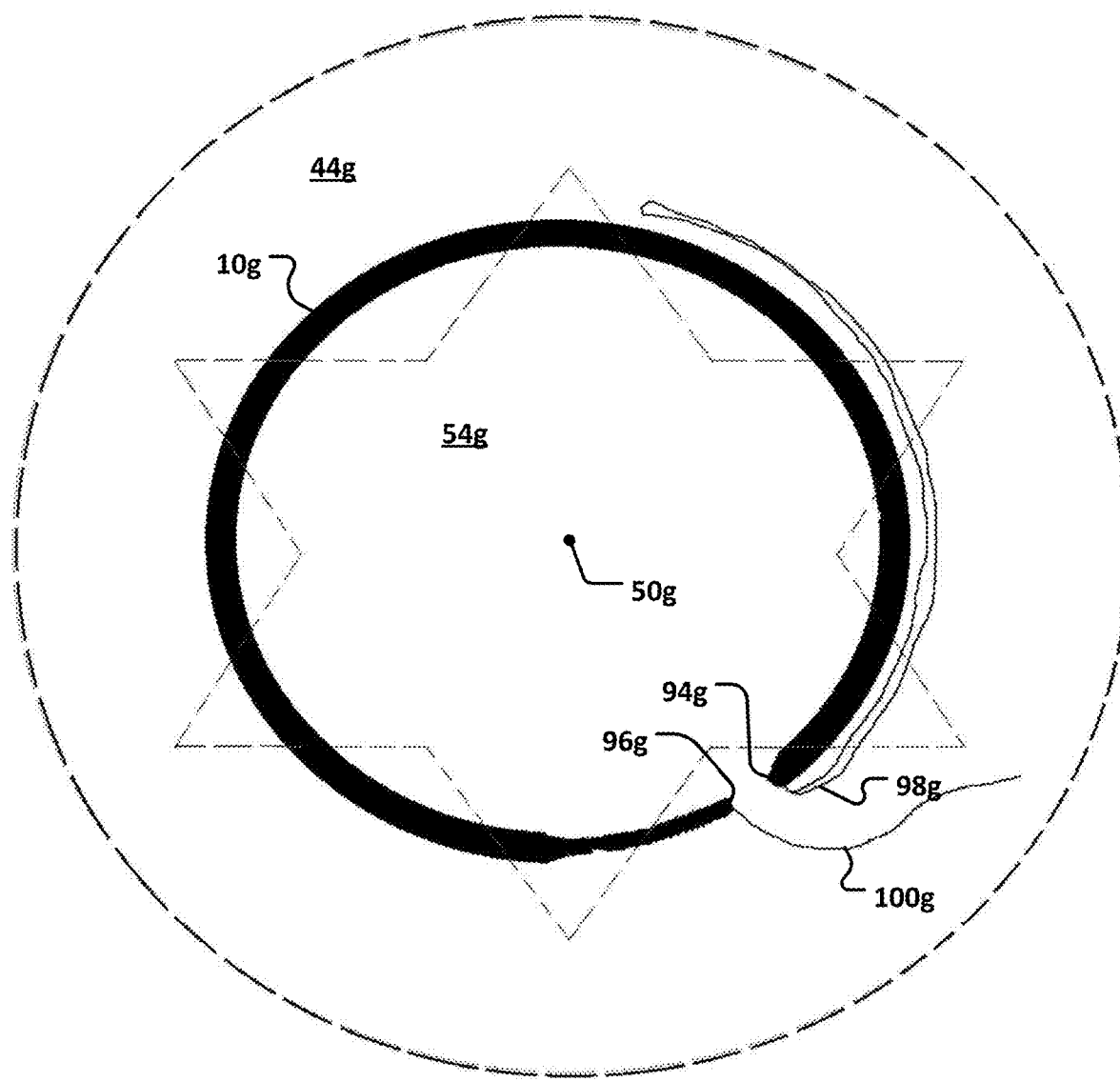
FIG. 24 is a second front view of the portion of the host cornea and the corneal graft shown in FIG. 23 with both structures shown in phantom and a prosthesis which was not visible in FIG. 23 shown in solid line and is associated with a first exemplary method provided by the present disclosure.

The present disclosure also provides various methods for using a prosthesis in combination with a suture. FIG. 23 is a front view of a portion of a host cornea 44g and a corneal graft 54g. FIG. 24 is a second front view of the portion of the host cornea 44g and the corneal graft 54g shown in FIG. 23 with both structures shown in phantom and a prosthesis 10g which was not visible in FIG. 23 shown in solid line. The prosthesis 10g is associated with a first exemplary method provided by the present disclosure.

The exemplary prosthesis/body 10g is discontinuous about an optic axis 50g and extends between a leading edge 94g and a trailing edge 96g. A first suture 98g is attached to the leading edge 94g of the body 10g and a second suture 100g is attached to the trailing edge 96g of the body 10g. The exemplary suture 98g is shown forming a loop. The suture 98g can be drawn through a first passageway in the host cornea 44g and a second passageway corneal graft 54g with the body 10g as the body 10g is positioned in those passageways. When the body 10g is positioned in both passageways, the suture 98g can be drawn or pulled out of the passageways and exposed for use. Next, the suture 98g and the second suture 100g can be tied together and thereby bring the leading edge 94g and trailing edge 96g together.

FIG. 25A-25D illustrate a series of images associated with a second exemplary method provided by the present disclosure. A suture 102g is attached to the leading edge 94g and also to the trailing edge 96g of the body 10g. The suture 102g can be drawn through a first passageway in the host cornea 44g and a second passageway corneal graft 54g with the body 10g as the body 10g is being positioned in those passageways, as shown in FIG. 25A. FIG. 25A also shows a portion 104g of the suture 102g exposed and not in the passageways. Next, a second portion 106g of the suture 102g can be drawn or pulled out of the passageways and exposed for use as shown in FIG. 25B. Then, the first portion 104g the suture 102g and the second portion 106g of the suture 102g can be tied together, as shown in FIG. 25C. The extraneous portions of the suture 102g can then be removed, as shown in FIG. 25C.

FIG. 26A-26D illustrate a series of images associated with a third exemplary method provided by the present disclosure. An exemplary suture 108g is attached to the leading edge 94g but not to the trailing edge 96g of the body

10g. The suture 108g can be drawn through a first passageway in the host cornea 44g and a second passageway corneal graft 54g with the body 10g as the body 10g is being positioned in those passageways. FIG. 26A also shows a trailing end portion 110g of the suture 108g exposed and not in the passageways. FIG. 26a also shows a second portion 112g of the suture 108g has been drawn or pulled out of the passageways and exposed for use. FIG. 26B shows the suture 108g separated from the body 10g after being drawn through the passageways. FIG. 26C shows the body 10g removed from the passageways after the suture 108g has been drawn through the passageways. FIG. 26D shows the portions 110g and 112g having been tied together and extraneous portions of the suture 108g removed.

In one or more embodiments of the present disclosure, a prosthesis/body that is discontinuous can be altered after being positioned in the passageways. A discontinuous prosthesis/body can at least partially overlap itself over a length after being positioned in the passageways. One example of overlap is shown in FIG. 4. Externally-generated energy, such as with a laser directed at the overlap, can be applied at a position along the length of overlap to weld portions of the prosthesis/body together and convert the prosthesis/body from discontinuous to continuous.

In one or more embodiments of the present disclosure, a prosthesis/body that is discontinuous or continuous can be altered after being positioned in the passageways. After being positioned, the prosthesis/body can define a circumferential tension or loop tension. Externally-generated energy, such as with a laser directed at some position along the prosthesis/body, can be applied to change the circumferential tension. The laser can be directed at one or more points such as points 78 shown in FIGS. 1 and 2. The prosthesis/body can be formed from different kinds of material so that the application of energy could increase the circumferential tension or decrease the circumferential tension. A particular embodiment of a prosthesis/body could be formed from more than one kind of material so that a first portion of the prosthesis/body could be altered to increase the circumferential tension and a second portion of the prosthesis/body could be altered to decrease the circumferential tension.

In one or more embodiments of the present disclosure, a prosthesis/body that is discontinuous or continuous can be altered in other ways after being positioned in the passageways. A prosthesis/body in one or more embodiments can extend along a central longitudinal axis and defines a width transverse to the central longitudinal axis. Exemplary width 18 is referenced in FIG. 1. Externally-generated energy, such as with a laser directed at some position along the prosthesis/body, can be applied to change the width at that position. The laser can be directed at one or more points such as points 78 shown in FIGS. 1 and 2. The prosthesis/body can be formed from different kinds of material so that the application of energy could increase or decrease the width. A particular embodiment of a prosthesis/body could be formed from more than one kind of material so that a first portion of the prosthesis/body could be altered to increase the width and a second portion of the prosthesis/body could be altered to decrease the width.

In one or more embodiments of the present disclosure, a continuous version of the prosthesis that can be placed in trench-like passageways (fashioned in the corneal stroma with openings to the external surface) that connects the host and donor tissues, with the assembly of the prosthesis and donor tissue held in close apposition to the host tissue by virtue of intraocular pressure. The disclosure of FIGS. 11, 18 and 19 described versions of such embodiments and it is noted that all combinations of passageway configurations shown in the other Figures of the present disclosure could be applied in such embodiments.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. The right to claim elements and/or subcombinations that are disclosed herein is hereby unconditionally reserved. The use of the word "can" in this document is not an assertion that the subject preceding the word is unimportant or unnecessary or "not critical" relative to anything else in this document. The word "can" is used herein in a positive and affirming sense and no other motive should be presumed. More than one "invention" may be disclosed in the present disclosure; an "invention" is defined by the content of a patent claim and not by the content of a detailed description of an embodiment of an invention.

What is claimed is:

1. A method of implanting a corneal prosthesis configured to be implanted in a cornea of an eye to interconnect host tissue with a corneal graft, the method comprising:
   forming an opening in a host tissue of an eye;
   forming a perimeter of a corneal graft;
   forming a first passageway through the host tissue that extends annularly about an optic axis of the eye;
   forming a second passageway through the corneal graft that extends annularly about an axis of the corneal graft that is substantially collinear with the optic axis of the eye when said corneal graft is finally positioned in the eye, the first passageway and the second passageway having the same diameter relative to the optic axis;
   arranging the corneal graft and the host tissue relative to one another;
   aligning the first passageway and the second passageway whereby the first passageway and the second passageway are in communication with one another;
   positioning a corneal prosthesis, having a ring-shaped body extending between a first end defining a leading edge and a second end defining a trailing edge and also having a first suture attached to the leading edge and also having a second suture attached to the trailing edge, in the first passageway and the second passageway;
   drawing the first suture through the first passageway and the second passageway with the ring-shaped body during said positioning,
   drawing out the first suture from the first and second passageways when the ring-shaped body is positioned in both passageways; and
   tying the first suture and the second suture together after said drawing out and thereby bring the leading edge and trailing edge together.

2. The method of claim 1 wherein:
   said forming the opening in the host tissue of the eye is further defined as forming the opening to include a first plurality of flaps in the host tissue positioned about the optic axis and extending toward the optic axis;

said forming the perimeter of the corneal graft is further defined as forming the perimeter to include a second plurality of flaps in the corneal graft positioned about the optic axis and extending away from the optic axis when the corneal graft is finally positioned in the eye; and said method further comprises:

arranging the corneal graft and the host tissue relative to one another such that the first plurality of flaps and the second plurality of flaps circumferentially and alternatingly overlap about the optic axis when the corneal graft is finally positioned in the eye.

* * * * *